United States Patent
Lundmark et al.

(10) Patent No.: US 6,365,143 B1
(45) Date of Patent: Apr. 2, 2002

(54) CLEANSING COMPOSITION AND METHOD FOR REMOVING CHEMICALLY BOUND RESIDUES AND MINERAL DEPOSITS FROM HAIR

(76) Inventors: Larry D. Lundmark, 7540 Orchid La. N., Maple Grove, MN (US) 55311; Wallace R. Hlavac, 1201 Yale Pl., Minneapolis, MN (US) 55403

( * ) Notice: Subject to any disclaimer, the term of this patent is extended or adjusted under 35 U.S.C. 154(b) by 0 days.

(21) Appl. No.: 09/541,918

(22) Filed: Apr. 3, 2000

(51) Int. Cl.$^7$ .......................... A61K 7/06; A61K 7/075
(52) U.S. Cl. ................ 424/70.22; 424/70.1; 424/70.24
(58) Field of Search ........................... 424/70.1, 70.24, 424/70.22

(56) References Cited

U.S. PATENT DOCUMENTS 5,073,545 A * 12/1991 Arima et al.
5,540,853 A * 7/1996 Trinh et al.
5,635,167 A * 6/1997 Said et al.
5,804,172 A * 9/1998 Ault
5,853,706 A * 12/1998 Klar \* cited by examiner Primary Examiner—Thurman K. Page
Assistant Examiner—S. Howard
(74) Attorney, Agent, or Firm—Forrest L. Collins

(57) ABSTRACT

An alkaline composition for use in removal of mineral deposits and cationic polymeric buildup from hair is disclosed herein. Said composition comprises the combination of a multidentate ligand complex, an anionic polysulfonate salt and water. A synergistic combination of chelating agents is disclosed which has been found to be highly effective in removing bound minerals from hair at a slightly alkaline pH. Also disclosed is a composition for simultaneously removing bound residues and mineral deposits from hair.

24 Claims, No Drawings

CLEANSING COMPOSITION AND METHOD FOR REMOVING CHEMICALLY BOUND RESIDUES AND MINERAL DEPOSITS FROM HAIR

BACKGROUND

The present invention relates to the field of hair treatment and particularly to the removal of chemically bound residues and mineral deposits from hair. Hair may act as a sink for environmental minerals and heavy metals. In addition to undesirable changes in color and appearance, environmental minerals may have an adverse effect on chemical hair treatments. Mineral deposits in tap water may strip away highlights, darkening hair color to a brassier hue.

The phenomenon of blonde hair acquiring a green tint when exposed to swimming pool water containing copper has been attributed to copper mineral absorption by hair. Such absorption occurs when copper is in the form of a weak complex of copper sulfate. Subsequent shampooing with a conventional composition cannot strip the green color. (Reference. G. Ramachandra Bhat, et. al., *J.Soc. Cosmet. Chem.*, 30, 1–8 (January/February 1979).

Previous attempts to develop compositions for the removal of minerals from human hair have utilized high concentrations of known chelating agents, extended contact times and processes which require the application of heat. In addition, special packaging may be required to prevent decomposition in the presence of air. For example, Ault in U.S. Pat. No. 5,804,172 issued Sep. 8, 1998 discloses a composition for use in removal of minerals from hair which comprises the combination of an acidifying agent, a reducing agent, a chelating agent, a gelling agent and water. A synergistic combination of chelating agents is stated to be disclosed in the Ault patent. Also disclosed in the Ault patent is a process for packaging the compositions and a method for removal of mineral residues from hair by the use of such compositions. The method disclosed in the Ault patent for the removal of mineral residues from hair may take up to 45 minutes for the removal of iron from hair. It is also stated in the Ault patent that the process requires the application of heat and an airtight container to prevent oxidation that would negate the usefulness of the invention.

U.S. Pat. No. 5,635,167 to Said, et al., issued Jun. 3, 1997 discloses a process for the removal of exogenous metal ions attached to human hair or keratin fiber which include the steps of contacting at least one chelating agent to the human hair or keratin fiber, the chelating agent selected from the group consisting of amino acid-type, polyphosphate-type and phosphonate-type agents, maintaining contact with the chelating agent and the human hair or keratin fiber for a period of time sufficient to permit the chelating agent to complex with the exogenous minerals, thereby removing at least a portion of the attached minerals, and rinsing the chelating agent.

The process of the Said, et al., patent is enhanced with the pH adjusted to a range of between 4 to 9, preferably 5 to 8. The chelating agent of the Said, et al., patent is added at a concentration of 4% by weight to 25% by weight, preferably 5 to 20% by weight. In a preferred case, the chelating agent is selected from the group consisting of a salt of ethylenediamine-tetraacetic acid, a salt of hydroxyethylethylenediaminetriacetic acid, a salt of diethylenetriaminepentaacetic acid, a salt of nitrilotriacetic acid and a salt of tripolyphosphate, preferably the sodium salt.

The Said, et al., patent teaches high concentrations of polyphosphate or phosphonate which may be irritating to the scalp of certain sensitive individuals and may limit the utility of the proposed invention for use in low irritation shampoo compositions.

Gary, et al., in U.S. Pat. No. 3,998,761 issued Dec. 21, 1976 discloses a shampoo composition suitable for conditioning hair. The compositions of the Gary, et al., patent comprise at least one detergent and a waste liquid beer sludge concentrate distributed in an aqueous medium. The beer solids are stated to be, in the Gary, et al., patent composition at from about 4% to 20% by weight based on the total weight of the shampoo composition and wherein said detergent comprises about 10 to 20% based on the total weight of the composition. The compositions of the Gary, et al., patent may contain minor amounts of proteins.

U.S. Pat. No. 4,581,229 issued to Petrow on Apr. 8, 1986 discloses a hair treating solution and method which is stated to provide for improving hair quality and aiding in removal of inorganic substances from hair. The Petrow patent states that metals such as copper, iron, manganese, nickel and the like, if attached to hair after swimming or other hair-exposure thereto, can be removed by the use of a soluble lanthanum salt in a simple rinsing method.

The coloring of hair to a desired shade and having the hair retain the desired shade is quite important to consumers as set out in U.S. Pat. No. 5,112,359 Murphy, et al., issued May 12, 1992. The Murphy, et al., patent discloses certain dispersant free substituted diaminoanthaquinone (sic) colorants stated to be useful in hair dye compositions to more intensely color hair. The Murphy, et al., patent states that coloring kits, mousses, gels, and aerosols may contain the compositions disclosed therein.

Cationic polymers are used in shampoos and conditioners to facilitate combability and to make the hair feel softer and smoother to the touch. Cationic surfactants are positively charged molecules that have an affinity for negatively charged sites on the hair. When used repeatedly, an excess of cationic polymer may buildup on the hair shaft, resulting in dull, lifeless hair. Compositions for the removal of minerals from human hair do not address the problem of cationic polymeric buildup on the hair shaft.

U.S. Pat. No. 4,412,026 issued to Collins Oct. 25, 1983 discusses polymeric compositions, and in particular, the homopolymeric salt of 2-acrylamido-2-methylpropanesulfonic acid in an amount to sufficient to thicken the compositions disclosed therein.

Throughout the specification and claims, percentages and ratios are by weight, and temperatures are in degrees Celsius unless otherwise indicated. To the extent that any of the references cited herein are applicable, they are hereby specifically incorporated by reference. Ranges and ratios given herein may be combined.

SUMMARY OF THE INVENTION

The present invention describes a composition suitable for removing deposits from hair comprising:

(a) an amino acetic acid;

(b) a member selected from the group consisting of a salt of ethylenediaminetetraacetic acid, a salt of hydroxyethylethylenediaminetriacetic acid, and a salt of diethylenetriaminepentaacetic acid, and mixtures thereof;

(c) citric acid; and, (d) water.

A further aspect of the present invention is a composition which is the reaction product of a mixture comprising:

(a) glycine;

(b) a member selected from the group consisting of a salt of ethylenediaminetetraacetic acid, a salt of hydroxyethylethylenediaminetriacetic acid, and a salt of diethylenetriaminepentaacetic acid, and mixtures thereof;

(c) citric acid; and, (d) water.

Yet a further aspect of the present invention is a method for removing chemically bound residues and/or mineral deposits from hair upon the head by applying a sufficient amount of a composition comprising:

(a) an amino acetic acid;

(b) a member selected from the group consisting of a salt of ethylenediaminetetraacetic acid, a salt of hydroxyethylethylenediaminetriacetic acid, and a salt of diethylenetriaminepentaacetic acid, and mixtures thereof;

(c) citric acid; and, (d) water;

for a sufficient time to remove residues and/or mineral deposits from hair upon the head.

DETAILED DESCRIPTION OF THE INVENTION

For the purposes of promoting an understanding of the principles of the invention, reference will now be made to the preferred embodiment. No limitation of the scope of the invention is thereby intended for further applications of the principles of the invention, which would normally occur or be contemplated by one skilled in the art to which the invention relates.

One aspect of the present invention relates to a composition and method for removing chemically bound minerals from hair comprising a multidentate ligand complex and water in a weakly alkaline environment. The complex is formed by adding glycine to an alkaline solution of a member selected from the group consisting of a salt of ethylenediaminetetraacetic acid, a salt of hydroxyethylethylenediaminetriacetic acid, and a salt of diethylenetriaminepentaacetic acid, and mixtures thereof. Preferably, the salt is the tetrasodium salt of ethylenediaminetetraacetic acid (EDTA) followed by the addition of citric acid to a weakly alkaline pH of approximately 7.5. The resultant "citrified glycine edetate" composition has been found to be highly effective in removing bound environmental minerals by a unique hair penetration and chelation process.

It is understood that while citric acid is the preferred ingredient, that any material capable of generating citric acid is included within the definition of citric acid. Thus, citrate salts such as sodium citrate may be employed herein.

Chelation is a chemical reaction or process involving chelate ring formation and is characterized by multiple bonding between two or more of the electron-pair-donor groups of a multidentate ligand and electron-pair-acceptor metal ion.

It is an object of the present invention to provide a synergistic composition suitable for removing minerals from hair, which includes the tetrasodium salt of amino acetic acid (glycine), and the tetrasodium salt of ethylenediaminetetraacetic acid neutralized to a weakly alkaline pH with citric acid.

It is another object of the present invention to provide a process for simultaneously removing minerals and cationic surfactant and/or polymer buildup with a composition containing the tetrasodium salt of amino acetic acid and the tetrasodium salt of ethylenediaminetetraacetic acid neutralized to a weakly alkaline pH with an anionic polymer such as polyacrylamidomethylpropane sulfonic acid. It is theorized that the sulfonic acid portion of the polymer molecule and amino acetic acid forms hydrogen bonds with the tetrasodium salt of ethylenediaminetetraacetic acid forming a polyglycine edetate complex.

Hair is an assembly of fibers that contain proteins, which may bind minerals by both ionic bonds and covalent bonds. Cationic surfactants and polymers are positively charged molecules, which have an affinity for negatively charged sites on the hair. Undesirable buildup on hair fiber surfaces may result when certain types of cationic surfactants and polymers are used repeatedly to condition the hair.

The inventive compositions include three ingredients: aminoacetic acid (glycine), a member selected from the group consisting of a salt of ethylenediaminetetraacetic acid, a salt of hydroxyethylethylenediaminetriacetic acid, and a salt of diethylenetriaminepentaacetic acid, and mixtures thereof; and citric acid at a weakly alkaline pH. The resultant "citrified sodium glycinate edetate" complex appears to be capable of penetrating into the peripheral region of the hair fiber where absorbed minerals, such as copper, are primarily located. The weakly alkaline environment is advantageous to the promotion of cuticle swelling, thereby enhancing penetration of the chelating complex.

The inventive composition is preferably applied to the hair as a spray followed by shampooing for mineral removal. An alternative approach is to incorporate the glycinated chelating complex directly into a shampoo or hair conditioner for mineral removal. When an anionic polysulfonate salt is included in cleansing compositions containing the glycinated-chelating complex, the removal of undesirable buildup on hair fiber surfaces is also facilitated.

What follows is suggested exemplification of the present invention.

EXAMPLE 1

A citrified sodium glycinate edetate complex is formed by dissolving glycine in water, followed by the addition of the tetrasodium salt of ethylenediaminetetraacetic acid and citric acid to a pH of 7.50

|  | % by weight |
|---|---|
| Distilled water | 90.43 |
| Dissolvine ®100-S (Tetrasodium EDTA) | 5.60 |
| Glycine | 3.50 |
| Citric Acid | 0.42 |
| Kathon ® CG (preservative) | 0.05 |
|  | 100.00 |

The above complex was clear and uniform after mixing the above ingredients at 25° C.

EXAMPLE 2

A clarifying shampoo is prepared containing citrified sodium glycinate edetate complex.

|  | % by weight |
|---|---|
| Distilled water | 44.02 |
| Sodium Laureth Sulfate (Sulfochem ® ES2) | 35.00 |
| Cocamidopropyl Betaine (Lexaine ® C) | 7.00 |
| Sodium Lauroyl Sarcosinate (Hamposyl ® L-30) | 3.00 |
| DL Panthenol | 0.12 |

-continued

| | % by weight |
|---|---|
| Glycine | 3.50 |
| Tetrasodium EDTA (Dissolvine ® 100-S) | 5.60 |
| Citric Acid | 0.40 |
| Sodium Chloride | 1.00 |
| Fragrance | 0.31 |
| Kathon ® CG (preservative) | 0.05 |
| | 100.00 |

The above shampoo base is clear and uniform and has a pH of 7.30.

EXAMPLE 3

Green Color Copper Removal Test

The phenomenon of blonde hair acquiring a green tint when exposed to swimming pool water containing copper has been attributed to the formation of a weak copper complex in the hair shaft. Oxidation of the hair enhances copper absorption. Blonde hair which has been damaged by a perming (permanent waving) process and/or a hydrogen peroxide bleaching process, is especially susceptible to rapid uptake of copper. This causes the damaged blonde hair to take on a green coloration, which cannot be removed by a conventional shampoo cleansing process.

Damaged blonde hair, which has been permed and bleached, may be soaked in a solution of copper sulfate and sodium hypochlorite bleach to simulate extreme green hair uptake conditions in the laboratory. When damaged blonde green hair is shampooed and rinsed with the formula shown in Example 1, the green hair coloration is removed demonstrating copper mineral complex removal from the hair shaft. When damaged blonde green hair was shampooed with a control composition without complex, the green coloration was not removed.

EXAMPLE 4

An environmental mineral hair clarifying spray is prepared containing citrified sodium glycinate edetate complex and the anionic polymer, sodium polystyrene sulfonate (Flexan® 130):

| | % by weight |
|---|---|
| Water | 84.48 |
| DL Panthenol | 0.12 |
| Sodium Polystyrene Sulfonate (Flexan ® 130) | 3.33 |
| Glycine | 3.50 |
| Tetrasodium EDTA (Dissolvine ® 100-S) | 5.60 |
| Citric Acid | 0.40 |
| Fragrance | 0.25 |
| Isoceteth-20 (ARLSOLVE ® 200L) | 1.00 |
| DMDM ® hydatoin (Glydant) | 0.30 |
| Germaben II ® (preservative) | 1.00 |
| | 100.00 |

The above clarifying spray is clear and uniform and is water-thin, suitable for spraying as a mist.

EXAMPLE 5

Damaged green hair, which was used in Example 3, is sprayed with the composition shown in Example 4. After the shampooing and rinsing with the control shampoo without the glycinated used in Example 3, the green color is removed. The clarifying spray can therefore be used as a pretreatment on green hair to facilitate copper complex removal by using conventional shampoos which do not contain the citrified sodium glycinate edetate complex.

EXAMPLE 6

Cationic Surfactant and Polymer Buildup Removal Test

Generally, hair acquires an overall negatively charge in water. LUMICREASE BORDEAUX 3LR is a negatively charged polyazo sulfonate dye molecule, which is attracted to positively charged sites on hair and adsorbed cationic surfactants and polymers. The greater the dye adsorption, the greater the cationic charge density on the hair fiber surface. Dye adsorption (red-pink coloration) is therefore a function of cationic deposition and substantivity.

A damaged permed and bleached hair tress is soaked in a 1% solution of Polyquaternium-10® (a polymeric quaternary ammonium salt of hydroxyethyl cellulose reacted with a trimethyl ammonium substituted epoxide) to build up a cationic polymeric deposition upon the hair. The tress is then washed with the control shampoo composition, which did not contain citrified glycinated edetate complex or anionic polysulfonate polymer. The cycle was repeated five times. Hair fibers from the cationic polymeric buildup tress yield a positive red Lumicrease dye test result which indicates buildup tress are sprayed cationic polymeric buildup on the hair shaft.

Hair fibers from the cationic polymeric buildup with the clarifying mist formula shown in Example 4 followed by washing with the control shampoo composition that did not contain citrified glycinated edetate complex or anionic polysulfonate polymer. The hair fibers yield a negative Lumicrease dye test result (no red-pink coloration) which indicates that the cationic polymeric buildup has been removed.

EXAMPLE 7

Iron Removal Test

The presence of iron in the hair shaft may be observed with the aid of a light microscope and special staining techniques.

Damaged permed/bleached hair is especially prone to the uptake of iron. This may be demonstrated in the laboratory using hair which has been soaked in a solution of ferric chloride, followed by rinsing, staining and observations with a suitable light microscope.

Damaged permed/bleached hair fibers are soaked in 2% ferric chloride, rinsed and stained with 0.1 M potassium thiocyanate solution. A blood red iron complex forms that may be observed with a suitable light microscope.

The presence of iron in the hair shaft may also be visualized using light microscopy and a potassium ferrocyanide staining technique. Iron (ferric ion) forms a dark-blue complex in the presence of potassium ferrocyanide.

Damaged permed/bleached hair fibers are soaked in 2% ferric chloride followed by shampooing and rinsing using the clarifying shampoo composition shown in Example 2. The absence of a dark-blue color after uptake of 0. 1M potassium ferrocyanide solution indicates that the clarifying shampoo facilitates iron removal from hair.

Amounts of the Components

The compositions of the present invention contain the amino acetic acid, preferably glycine, at a concentration of 1.0 percent to about 5.0 percent by weight of the total composition. Preferably, the concentration of the amino acetic acid in the composition is from about 1.1 percent to about 4.0 percent by weight of the total composition.

The compositions of the present invention contain water at a concentration of about 10 percent to about 85 percent by weight of the total composition. Preferably, the concentration of the water is about 15 percent to about 80 percent by weight of the total composition.

The compositions of the present invention contain citric acid at a concentration of about 1.0 percent to about 15 percent by weight of the total composition. Preferably, the concentration of the citric acid, as citric acid, is about 1.2 percent to about 13 percent by weight of the total composition.

The compositions of the present invention have an alkaline pH. Preferably, the pH is about is about 7.01 to about 8.5, more preferably 7.1 to about 8.2

Composition Preparation

The composition is prepared by combining the various ingredients in a suitable mixing vessel. The mixing is continued for about one half-hour. Any remaining ingredients, including preservatives, fragrances and antimicrobial materials may be added at any point in the process where the added ingredient maintains its intended function and where the added ingredient does not interfere with the remainder of the composition.

Composition Utilization

For the best results it is suggested that the hair be wet when the composition is applied. Suitable surfactants (detergents) for cleaning the hair after applying the composition of the present invention are described below. The same surfactant materials will further remove residues from the hair.

The compositions of the present invention may be formulated into lotions, balms, and mousses or in conjunction with a shampoo or hair conditioners and the like. The level of usage in the finished products for consumer use is typically to apply the product at 0.1 grams to 50 grams per liter of liquid composition applied or directly upon the hair at 0.1 gram to 1 gram per 250 grams of hair. The products containing the compositions of the present invention is conveniently applied to the hair at room temperature to slightly elevated temperatures, e.g. 18 to 38 degrees Celsius.

Suitable anionic surfactants are those generally incorporated into a shampoo composition. Generally, the anionic surfactant is a water-soluble alkyl sulfate or alkyl aryl sulfonate having from about 8 to about 22 carbons, preferably from about 12 to about 18 carbons in the alkyl radical, which may be straight or branched chain, and also includes such classes of compounds which may be ethoxylated with from 1 to 5 moles, preferably 1 to 3 moles, ethylene oxide per molecule. The sulfate or sulfonate group is typically base-neutralized to provide an alkali metal cation, such as sodium or potassium, ammonium, or mono, di-, or trialkanolium cations.

Illustrative anionic surfactants of the above-named classes include: Sodium cetyl sulfate, sodium myristyl sulfate, sodium lauryl sulfate, sodium tallow sulfate, sodium decyl sulfate, sodium dodecylbenzene sulfonate, sodium tridecylbenzene sulfonate, sodium C 14 to C 16 olefin sulfonate, sodium C 12 to C 15 alcohol sulfate, sodium lauryl ether sulfate, sodium myristyl ether sulfate, sodium polyoxyethylene (5 moles ethylene oxide) lauryl ether sulfate, sodium polyoxyethylene (12 moles ethylene oxide) lauryl ether sulfate, sodium nonylphenyl ether sulfate, sodium polyoxyethylene (1 to 4 moles ethylene oxide), C 12 to C 15 alkyl ether sulfate, sodium lauryl sulfoacetate.

Synthetic anionic detergents useful herein include alkyl and alkyl ether sulfates. These materials have the respective formulae $ROSO_3M$ and $RO(C_2H_4O)_xSO_3M$ wherein R is alkyl or alkenyl of about 10 to about 20 carbon atoms, x is 1 to 10, and M is a water-soluble cation such as ammonium, sodium, potassium and triethanolamine. The alkyl ether sulfates useful in the present invention are condensation products of ethylene oxide and monohydric alcohols having about 10 to about 20 carbon atoms. Preferably, R has 14 to 18 carbon atoms in both the alkyl and alkyl ether sulfates. The alcohols can be derived from fats, e.g., coconut oil or tallow, or can be synthetic. Lauryl alcohol and straight chain alcohols derived from coconut oil are preferred herein. Such sulfated and neutralized alcohols are reacted with 1 to 10, and especially 3, molar proportions of ethylene oxide and the resulting mixture of molecular species have, for example, an average of 3 moles of ethylene oxide per mole of alcohol.

Specific examples of alkyl ether sulfates of the present invention are sodium coconut alkyl triethylene glycol ether sulfate; lithium tallow alkyl triethylene glycol ether sulfate; and sodium tallow alkyl hexaoxyethylene sulfate. Highly preferred alkyl ether sulfates are those comprising a mixture of individual compounds, said mixture having an average alkyl chain length of from about 12 to 16 carbon atoms and an average degree of ethoxylation of from about 1 to 4 moles of ethylene oxide. Such a mixture also comprises from about 0 to 20% by weight C 12–13 compounds; from 60 to 100% by weight of C 14–15–16 compounds, from about 0 to 20% by weight of C 17–18–19 compounds; from about 3 to 30% by weight of compounds having a degree of ethoxylation of 0; from about 45 to 90% by weight of compounds having a degree of ethoxylation of from 1 to 4; from about 10 to 25% by weight of compounds having a degree of ethoxylation of from 4 to 8; and from about 0.1 to 15% by weight of compounds having a degree of ethoxylation greater than 8.

Other suitable anionic detergents utilizable herein are olefin sulfonates having about 12 to about 24 carbon atoms. The term "olefin sulfonates" is used herein to mean compounds which can be produced by the sulfonation of an alpha-olefin by means of uncomplexed sulfur trioxide, followed by neutralization of the acid reaction mixture in conditions such that any sultones which have been formed in the reaction are hydrolyzed to give the corresponding hydroxyalkane sulfonates. The sulfur trioxide can be liquid or gaseous, and is usually, but not necessarily, diluted by inert diluents, for example by liquid $SO_2$, when used in the liquid form, or by air, nitrogen, gaseous $SO_2$, etc., when used in the gaseous form.

The alpha-olefin sulfonates useful herein are derived from mono-olefins having 12 to 24 carbon atoms, preferably 14 to 16 carbon atoms. Preferably, they are straight chain olefin. Examples of suitable 1-olefin include 1-dodecene; 1-tetradecene; 1-hexadecene; 1-octadecene; 1-cicosene and 1-tetraeosene.

Additional surfactant materials, which may be utilized herein, include the following exemplified materials: Long Chain tertiary amine oxides corresponding to the following general formula:

$R^1R^2R^3NO$ wherein $R^1$ contains an alkyl, alkenyl or monohydroxy alkyl radical of from about 8 to about 18 carbon atoms, from 0 to about 10 ethylene oxide moieties, and from 0 to 1 glyceryl moiety, and $R^2$ and $R^3$ contain from 1 to about 3 carbon atoms and from 0 to about 1 hydroxy group, e.g., methyl, ethyl, propyl, hydroxy ethyl, or hydroxy propyl radicals. The arrow in the formula is omitted as it is a conventional representation of a semi-polar bond between the nitrogen and the oxygen.

Examples of amine oxides suitable for use in this invention include dimethyldodecylamine oxide, oleyldi(2-hydroxyethyl)amine oxide, dimethyloctylamine oxide, dimethyldecylamine oxide, dimethyltetradecylamine oxide, 3,6,9-trioxaheptadecyldiethylamine oxide, di(2-hydroxyethyl)-tetradecylamine oxide, 2-dodecoxy-ethyldimethylamine oxide, 3-dodecoxy-2-hydroxypropyldi(3-hydroxy-propyl) amine oxide, and dimethyl-hexadecylamine oxide.

Further additional surfactants include long chain tertiary phosphine oxides corresponding to the following general formula:

RR'R"PO wherein R contains an alkyl, alkenyl or monohydroxyalkyl radical ranging from 8 to 18 carbon atoms in chain length, from 0 to about 10 ethylene oxide moieties and from 0 to 1 glyceryl moiety and r' and r" are each alkyl or monohydroxyalkyl groups containing from 1 to 3 carbon atoms. The arrow in the formula is omitted, as it is a conventional representation of a semi-polar bond between the phosphorus and the oxygen.

Optional Ingredients

The products containing the compositions described herein can contain a variety of nonessential optional components suitable for rendering such compositions more cosmetically acceptable. Such conventional optional ingredients are well known to those skilled in the art, e.g., pearlescent aids such as ethylene glycol distearate; preservatives such as benzyl alcohol, methyl paraben, propyl paraben and imidazolidinyl urea.

Further optional ingredients include conditioning agents such as cationic surfactants. Examples of cationic surfactants include tricetyl methyl ammonium chloride, cetyl trimethyl ammonium chloride, stearyldimethyl benzyl ammonium chloride, and di-(partially hydrogenated tallow) dimethylammonium chloride. The compositions of the present invention are compatible with a conditioning agent.

Additional ingredients include thickeners and viscosity modifiers such as a diethanolamide of a long chain fatty acid (e.g., PEG 3 Lauramide DEA) cocomonoethanolamide, amine oxides, block polymers of ethylene oxide and propylene oxide such as Pluronic F88 offered by BASF Wyandotte, fatty alcohols such as cetearyl alcohol, sodium chloride, sodium sulfate, polyvinyl alcohol, and ethyl alcohol; pH adjusting agents such as citric acid, sodium citrate, succinic acid, phosphoric acid, sodium hydroxide, sodium carbonate, etc., perfumes; dyes; and, sequestering agents. Such agents generally are used individually at a level of from about 0.01% to about 10%, preferably from about 0.5% to about 5.0% by weight of the composition.

What is claimed is:

1. A composition suitable for removing deposits from hair consisting essentially of:
    (a) an amino acetic acid;
    (b) a member selected from the group consisting of a salt of ethylenediaminetetraacetic acid, a salt of hydroxyethylethylenediaminetriacetic acid, and a salt of diethylenetriaminepentaacetic acid, and mixtures thereof;
    (c) citric acid; and,
    (d) water.

2. The composition of claim 1 wherein the amino acetic acid is present at a concentration of 1.0 percent to about 5.0 percent by weight of the total composition.

3. The composition of claim 1 wherein the pH is from about 7.01 to about 8.5.

4. The composition of claim 1 wherein the amino acetic acid is glycine which is present at a concentration of 1.0 to about 5.0 percent by weight of the total composition.

5. The composition of claim 1 further comprising an anionic polysulfonate surfactant.

6. The composition of claim 1 further comprising a citric acid salt.

7. The composition of claim 1 wherein the aminoacetic acid is glycine.

8. The composition of claim 7 wherein the glycine is present at a concentration of 1.0 to about 5.0 percent by weight of the total composition.

9. The composition of claim 1 wherein the water is present at a concentration of about 10 percent to about 85 percent by weight of the total composition.

10. The composition of claim 1 wherein the member (b) is the tetrasodium salt of ethylenediaminetetraacetic acid is present at a concentration of about 1.0 percent to about 15 percent by weight of the total composition.

11. The composition of claim 1 wherein the citric acid is present at a concentration of about 1.0 percent to about 15 percent by weight of the total composition.

12. A composition which is the reaction product of a mixture comprising:
    (a) glycine;
    (b) a member selected from the group consisting of a salt of ethylenediaminetetraacetic acid, a salt of hydroxyethylethylenediaminetriacetic acid, and a salt of diethylenetriaminepentaacetic acid, and mixtures thereof;
    (c) citric acid; and,
    (d) water.

13. The composition of claim 12 wherein the water is present at a concentration of about 10 percent to about 85 percent by weight of the total composition.

14. The composition of claim 12 wherein the member (b) is the tetrasodium salt of ethylenediaminetetraacetic acid is present at a concentration of about 1.0 percent to about 15 percent by weight of the total composition.

15. The composition of claim 12 wherein the citric acid is present at a concentration of about 1.0 percent to about 15 percent by weight of the total composition.

16. The composition of claim 12 wherein component (b) is salt is tetrasodium salt of ethylenediaminetetraacetic acid.

17. A method for removing chemically bound residues and/or mineral deposits from hair upon the head by applying a sufficient amount of a composition comprising:
    (a) an amino acetic acid;
    (b) a member selected from the group consisting of a salt of ethylenediaminetetraacetic acid, a salt of hydroxyethylethylenediaminetriacetic acid, and a salt of diethylenetriaminepentaacetic acid, and mixtures thereof;
    (c) citric acid; and,
    (d) water For a sufficient time to remove residues and/or mineral deposits from hair upon the head.

18. The method of claim 17 wherein the composition is applied to wet hair.

19. The method of claim 17 wherein the composition is applied to the hair, left in the hair and subsequently shampooing the hair within two hours of applying the composition to the hair.

20. The method of claim 17 wherein the composition is applied to the hair at a level 0.1 gram to 1 gram per 250 grams of hair.

21. The method of claim 17 wherein the composition is sprayed onto the hair.

22. The method of claim 17 wherein the component (a) is glycine.

23. The composition of claim 1 further comprising a surfactant selected from the group consisting of sodium laureth sulfate, sodium cocamidopropyl betaine and sodium lauroyl sarcosinate, and mixtures thereof.

24. The composition of claim 12 wherein the glycine is present at a concentration of 1.0 percent to about 5.0 percent by weight of the total composition.

* * * * *